(12) United States Patent
Sogo et al.

(10) Patent No.: US 9,497,360 B2
(45) Date of Patent: Nov. 15, 2016

(54) ELECTRODE INSPECTION APPARATUS FOR SPOT WELDING

(71) Applicants: KEYLEX CORPORATION, Hiroshima (JP); KYOKUTOH CO., LTD., Aichi (JP)

(72) Inventors: Kenji Sogo, Hiroshima (JP); Toshimasa Yamane, Hiroshima (JP); Yoshiaki Yamane, Hiroshima (JP); Kotaro Nakajima, Aichi (JP)

(73) Assignees: KEYLEX CORPORATION, Hiroshima (JP); KYOKUTOH CO., LTD., Aichi (JP)

(*) Notice: Subject to any disclaimer, the term of this patent is extended or adjusted under 35 U.S.C. 154(b) by 253 days.

(21) Appl. No.: 14/337,295

(22) Filed: Jul. 22, 2014

(65) Prior Publication Data

US 2014/0333756 A1 Nov. 13, 2014

Related U.S. Application Data

(63) Continuation of application No. PCT/JP2012/008078, filed on Dec. 18, 2012.

(30) Foreign Application Priority Data

Feb. 1, 2012 (JP) .................................. 2012-019562
Feb. 9, 2012 (JP) .................................. 2012-026036
Feb. 16, 2012 (JP) .................................. 2012-032052

(51) Int. Cl.
*H04N 5/225* (2006.01)
*B23K 11/11* (2006.01)
(Continued)

(52) U.S. Cl.
CPC ............ *H04N 5/2253* (2013.01); *B23K 11/11* (2013.01); *B23K 11/115* (2013.01); *B23K 11/252* (2013.01); *B23K 11/3063* (2013.01); *B23K11/36* (2013.01); *B23K 31/12* (2013.01); *G01N 21/8806* (2013.01); *H04N 5/2257* (2013.01); *G01N 21/94* (2013.01)

(58) Field of Classification Search
None
See application file for complete search history.

(56) References Cited

U.S. PATENT DOCUMENTS 6,201,206 B1    3/2001  Kitamura
8,648,903 B2*   2/2014  Loipetsberger ...... B23K 11/252
                                              219/109

(Continued)

FOREIGN PATENT DOCUMENTS

CN       1251548 A       4/2000
JP       01-192486 A     8/1989
WO       WO 2011/052308 A1   5/2011

OTHER PUBLICATIONS

International Search Report for corresponding International Application No. PCT/JP2012/008078 mailed Apr. 2, 2013.

(Continued)

*Primary Examiner* — Andy Rao
*Assistant Examiner* — Tyler Edwards
(74) *Attorney, Agent, or Firm* — Renner, Otto, Boisselle & Sklar, LLP

(57) ABSTRACT

A small camera module is simply assembled in a short time, while reducing displacement of a camera relative to the first and second frames. Specifically, the camera module is assembled by bending a pair of clips to engage engaging portions of the clips with engaging recesses of the first and second frames to fix the first frame, camera holders, and the second frame, with the first and second frames located at both sides of each camera holder with a housing recess facing outward, and using resilient force of each of the clips to press the camera with a projection of the clip.

9 Claims, 9 Drawing Sheets

(51) Int. Cl.

| | | |
|---|---|---|
| *B23K 11/30* | (2006.01) | |
| *B23K 11/36* | (2006.01) | |
| *B23K 11/25* | (2006.01) | |
| *B23K 31/12* | (2006.01) | |
| *G01N 21/88* | (2006.01) | |
| *G01N 21/94* | (2006.01) | |

(56) References Cited

U.S. PATENT DOCUMENTS

| | | | | |
|---|---|---|---|---|
| 2003/0218873 A1* | 11/2003 | Eromaki | ............ | H05K 9/0035 361/816 |
| 2008/0311782 A1* | 12/2008 | Nishio | ............ | H01R 12/716 439/357 |
| 2009/0173725 A1 | 7/2009 | Holcomb et al. | | |
| 2009/0289040 A1 | 11/2009 | Boyd | | |
| 2012/0200695 A1* | 8/2012 | Yamane | ............ | G01B 11/08 348/90 |

OTHER PUBLICATIONS

Form PCT/ISA/237 for corresponding International Application No. PCT/JP2012/008078 dated Apr. 2, 2013.

Extended European Search Report dated Nov. 16, 2015 for corresponding European Application No. 12867290.4.

\* cited by examiner

ELECTRODE INSPECTION APPARATUS
FOR SPOT WELDING

CROSS-REFERENCE TO RELATED
APPLICATIONS

This is a continuation of International Application No. PCT/JP2012/008078 filed on Dec. 18, 2012, which claims priority to Japanese Patent Application No. 2012-019562 filed on Feb. 1, 2012, Japanese Patent Application No. 2012-026036 filed on Feb. 9, 2012, and Japanese Patent Application No. 2012-032052 filed on Feb. 16, 2012. The entire disclosures of these applications are incorporated by reference herein.

BACKGROUND

The present disclosure relates to electrode inspection apparatuses for spot used in, for example, automobile production lines.

Conventionally, electrode inspection apparatuses for spot welding are used to properly manage electrodes mounted on the tips of guns for spot welding in automobile production lines. For example, International Patent Publication No. WO 2011/052308 (paragraphs [0070]-[0079] and FIGS. 15-18) shows an electrode inspection apparatus including measuring reference plates, each of which has an electrode fixing hole for inserting and fixing the tip of the electrode, and a camera module. The camera module includes a mirror reflecting the tip surface of the electrode, first and second frames located at the both sides of the mirror, a camera located at each side of the mirror between the first and second frames, and a camera holder having a housing recess for housing the camera. The camera module is assembled by placing the first and second frames at the both sides of the camera holder, with the opening of the housing recess facing outward. With each measuring reference plate attached to the camera module such that the electrode fixing hole corresponds to the mirror, the tip of the electrode is inserted into and fixed to the electrode fixing hole. The camera captures the tip surface of the electrode via the mirror to determine whether or not the tip surface of the electrode is usable.

SUMMARY

In the camera module, if the camera is displaced relative to the first and second frames, the positions of the images captured by the camera vary, thereby possibly causing erroneous determination of the electrode inspection apparatus. The camera needs to be thus firmly fixed to the first and second frames in assembling the camera module. International Patent Publication No. WO 2011/052308 (paragraph [0070]-[0079] and FIGS. 15-18) fails to show any fixing means of the components of the camera module.

Bonding with an adhesive and fastening with screws are considered as general means of fixing the components of a camera module. Bonding components with an adhesive is cumbersome, since attention needs to be paid not to cause seep-out of the adhesive. Fastening the components with screws is also cumbersome, since there is a need to form a plurality of fastening portions in the components. These fastening portions may increase the volume of the camera module. Fastening at the plurality of the fastening portions increases the time for assembly.

The present disclosure is made in view of the problems. It is an objective of the present disclosure to provide an electrode inspection apparatus for spot welding including a small camera module which can be simply assembled in a short time, and a camera which is not displaced relative to first and second frames after the camera module assembled.

In order to achieve the objective, the present disclosure allows a pair of clips to clip a plurality of components to fix the components.

A first aspect of the invention provides an electrode inspection apparatus for spot welding including measuring reference plates, each having an electrode fixing hole for inserting and fixing a tip of an electrode for spot welding; and a camera module. The camera module includes a mirror configured to reflect a tip surface of the electrode, a module body including first and second frames located at both ends of the mirror, a camera located at each side of the mirror between the first and second frames, and configured to capture the tip surface of the electrode reflected by the mirror, a camera holder having a housing recess for housing the camera, and a pair of flexible band-like clips. The camera module is assembled by bending the both clips to engage ends of the both clips with end edges of the first and second frames to fix the first frame, the camera holder, and the second frame, with the first and second frames placed at both sides of the camera holder with an opening of the housing recess facing outward, and using resilient force of each of the clips to press the camera in a middle of the clip. The tip of the electrode is inserted into and fixed to the electrode fixing hole, with each of the measuring reference plates attached to the camera module such that the electrode fixing hole corresponds to the mirror, and the camera captures the tip surface of the electrode via the mirror to determine whether or not the tip surface of the electrode is usable.

According to a second aspect of the present disclosure, in the electrode inspection apparatus for spot welding according to the first aspect, a projection is formed in the middle of each of the clips at a side close to the camera holder.

According to a third aspect of the present disclosure, in the electrode inspection apparatus for spot welding according to the first or second aspect, the camera module includes a pair of support frames configured to support both side end edges of the mirror, and interposed and fixed between the first and second frames.

According to a fourth aspect of the present disclosure, the electrode inspection apparatus for spot welding according to any one of the first to third aspects further includes a housing case configured to house the camera module. The camera module includes a transparent protective cover. The measuring reference plates are detachably attached to the housing case. Communicating openings corresponding to the mirror are formed in the housing case and the module body to face the electrode fixing hole of each of the measuring reference plates. The protective cover is interposed between each of the measuring reference plates and the housing case to cover the openings. A ring projection projects in a periphery of the electrode fixing hole of each of the measuring reference plates toward the housing case to form a thick portion. A fitting portion, in which the ring projection is fitted, is formed in a periphery of the opening of the module body.

According to a fifth aspect of the present disclosure, in the electrode inspection apparatus for spot welding according to any one of the first to fourth aspects, a protective cover is formed like a panel, and includes a recessed cover body fitted in an opening of the housing case, and a fitting portion of the module body, and an extension extending outward from a periphery of an opening end of the cover body, and sandwiched between each of the measuring reference plates and the housing case.

According to a sixth aspect of the present disclosure, the electrode inspection apparatus for spot welding according to any one of the first to fifth aspects further includes an opening-closing section located outside the protective cover, and configured to open and close the electrode fixing hole; and a control section connected to the camera and the opening-closing section, configured to output a capture operation signal to the camera and opening-closing operation signals to the opening-closing section. The control section outputs an opening operation signal to the opening-closing section to open the electrode fixing hole, outputs a capture operation signal to the camera with the electrode inserted into and fixed to the electrode fixing hole to capture the electrode tip surface with the camera via the mirror, processes an captured image of the tip surface of the electrode, and compares a result of processing with a predetermined value of the tip surface of the electrode to determine whether or not the electrode tip surface is usable. The control section outputs an closing operation signal to the opening-closing section to close the electrode fixing hole, outputs a capture operation signal to the camera to capture the protective cover with the camera via the mirror, processes an captured image of the protective cover, and compares a result of processing with a predetermined value of the protective cover to determine whether or not the protective cover is usable.

According to a seventh aspect of the present disclosure, in the electrode inspection apparatus for spot welding according to the sixth aspect, the opening-closing section is slidable to intersect a direction of inserting the electrode into the electrode fixing hole. A sliding operation switches the electrode fixing hole between an open position and a closed position.

According to an eighth aspect of the present disclosure, in the electrode inspection apparatus for spot welding according to the seventh aspect, the opening-closing section includes a housing space configured to house the housing case, to which the measuring reference plates are attached, from one side to a region including the electrode fixing hole, and a slidable cover case having an opening corresponding to the electrode fixing hole. The cover case performs sliding operation to move between a position in which the opening corresponds to the electrode fixing hole, and a position in which the opening deviates from the electrode fixing hole.

In the first aspect of the invention, the clips clip the first and second frames together to integrate the first frame, the camera holders, and the second frame. The middles of the clips press the cameras toward the camera holders with the first frame, the camera holders, and the second frame integrated. By using the clips as fixing means of the components of the camera module, the first and second frames are fixed to the camera holders, and the cameras are fixed to the camera holders at once. Only a short time is required to assemble the camera module, as compared to the case using an adhesive or screws. Since there is no need to form fastening portions in the components to fix the first frame, the camera holders, and the second frame together, the camera module can be miniaturized. After the camera module is assembled, the resilient force of the clips always presses the cameras toward the camera holders. In using the electrode inspection apparatus, the cameras are not displaced relative to the first and second frames, thereby causing no or less erroneous determination of the electrode inspection apparatus.

In the second aspect, since the tips of the projections of the clips abut on the cameras after the camera module is assembled, the projections reliably transmit the resilient force of the bent clips to the cameras, thereby fixing the cameras to the camera holders more firmly.

In the third aspect of the invention, when the clips clip the first and second frames, not only the camera holders but also the both support frames supporting the mirror are integrally fixed while being sandwiched between the first and second frames. Therefore, by using the clips to assemble the camera module, the mirror can be mounted between the first and second frames at the same time as fixing the first frame, the camera holders, and the second frame. As a result, the camera module is assembled more simply.

In the fourth aspect of the invention, when the measuring reference plates are attached to the housing case, the ring projections are fitted in the fitting portions formed in the camera module. That is, the positioning of the measuring reference plates is determined not with respect to the housing case but to the camera module. The electrode fixing holes are thus not displaced relative to the mirror, when the measuring reference plates are attached to the housing case after being detached from the housing case to exchange the protective covers. This does not change the positions of the tip surfaces of the electrodes, whose images are captured by the cameras, before and after exchanging the protective covers. No or less erroneous determination of the electrode inspection apparatus occurs due to the exchange of the protective covers. Furthermore, since the ring projections increase the thicknesses of the measuring reference plates in the peripheries of the electrode fixing holes, the stiffness of the thick portions increases to reduce deformation in abutting on the electrodes. The positioning of the electrodes does not change due to the deformation in the peripheries of the electrode fixing holes, thereby reducing positional changes of the tip surfaces of the electrodes, whose images are captured by the cameras. This also causes no or less erroneous determination of the electrode inspection apparatus.

In the fifth aspect of the invention, at the side close to the housing case, each measuring reference plate abuts the corresponding protective cover, with the measuring reference plate attached to the housing case. This allows less dust etc., to enter the housing case from the gap between each measuring reference plate and the protective cover, thereby reducing malfunction of the electrode inspection apparatus due to the dust etc., entering the housing case.

In the sixth aspect of the invention, the control device for determining whether or not the tip surfaces of the electrodes are usable is used to determine whether or not the protective covers are usable. As a result, the operator figures out the contamination degree of the protective covers outside the production line. Therefore, the protective covers can be exchanged at proper timing to reduce erroneous determination caused by excessive dirt of the protective covers. In addition, the production line is stopped for a minimum time period necessary for exchanging the protective covers, thereby reducing drop in the operating rate of the production line caused by the exchange of the protective covers. When the protective covers are captured with the electrode fixing holes covered with the opening-closing section, the opening-closing section serves as the background to clarify the captured images even if the protective covers are transparent. This allows the control section to analyze the images accurately, thereby reliably reducing erroneous determination.

Since the opening-closing section covers the electrode fixing holes, dust etc., is difficult to pass through the electrode fixing holes and enter the housing case. This retards contamination of the protective covers and reduces the time intervals of exchanging the protective covers, thereby increasing the operating rate of the production line.

In the seventh aspect of the invention, the opening-closing section slides to intersect the direction of inserting the electrodes into the electrode fixing holes. Even when the opening-closing section moves the electrode fixing holes from the closed positions to the open positions, with the electrodes placed near the electrode fixing holes, the electrodes do not abut on the opening-closing section. This reduces the period between the time of opening the electrode fixing holes with the opening-closing section and the time of inserting the electrodes into the electrode fixing holes. Furthermore, dust etc., is difficult to pass through the electrode fixing holes and enter the housing case, thereby retarding contamination of the protective covers.

In the eighth aspect of the invention, the cover case covers at least the region of housing case including the electrode fixing holes, and thus protects part or whole of the exterior. Furthermore, since the cover case for protecting the exterior of the housing case is used to open and close the electrode fixing holes, there is no need to add any components for opening and closing the electrode fixing holes other than the cover case. The structure is formed simply at low costs.

DETAILED DESCRIPTION

Embodiments of the present disclosure will be described hereinafter in detail with reference to the drawings. The following preferred embodiments are intrinsically mere examples.

First Embodiment

Figure 1:
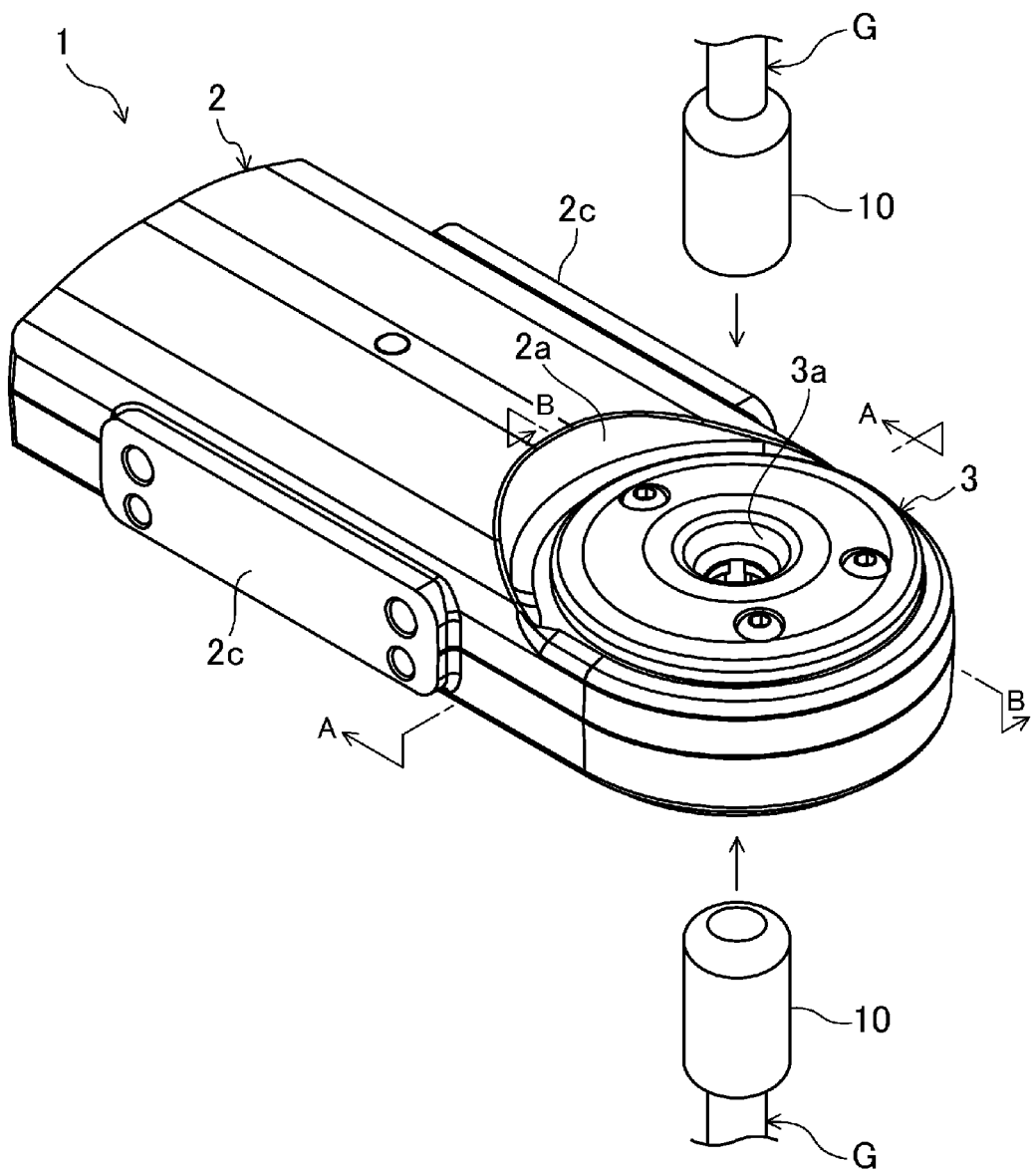
FIG. 1 is a perspective view of an electrode inspection apparatus for spot welding according to embodiments of the present disclosure.

FIG. 1 illustrates an electrode inspection apparatus 1 for spot welding according to a first embodiment of the present disclosure. This electrode inspection apparatus 1 inspects whether or not the tip surfaces of a pair of electrodes 10 are usable for spot welding of steel plates at the same time. The electrodes 10 are mounted on and held by the tips of a pair of weld guns G facing vertically. The electrode inspection apparatus 1 includes a flat cuboid metal housing case 2. The surface of the housing case 2 curves gently such that the middle of the line horizontally intersecting the longitudinal direction of the housing case 2 is located at the top.

Figure 2:
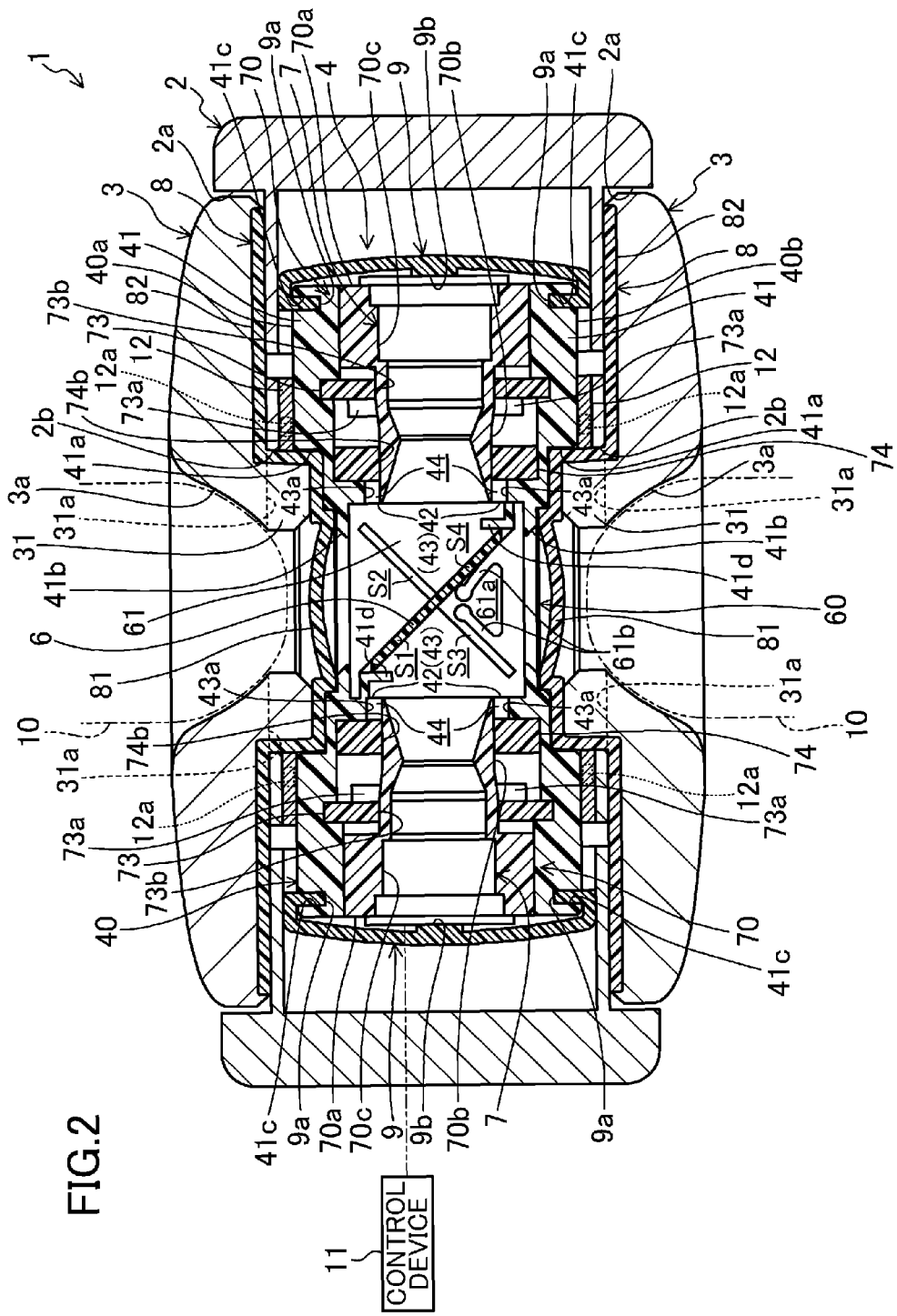
FIG. 2 is a cross-sectional view taken along the line A-A of FIG. 1.
Figure 3:
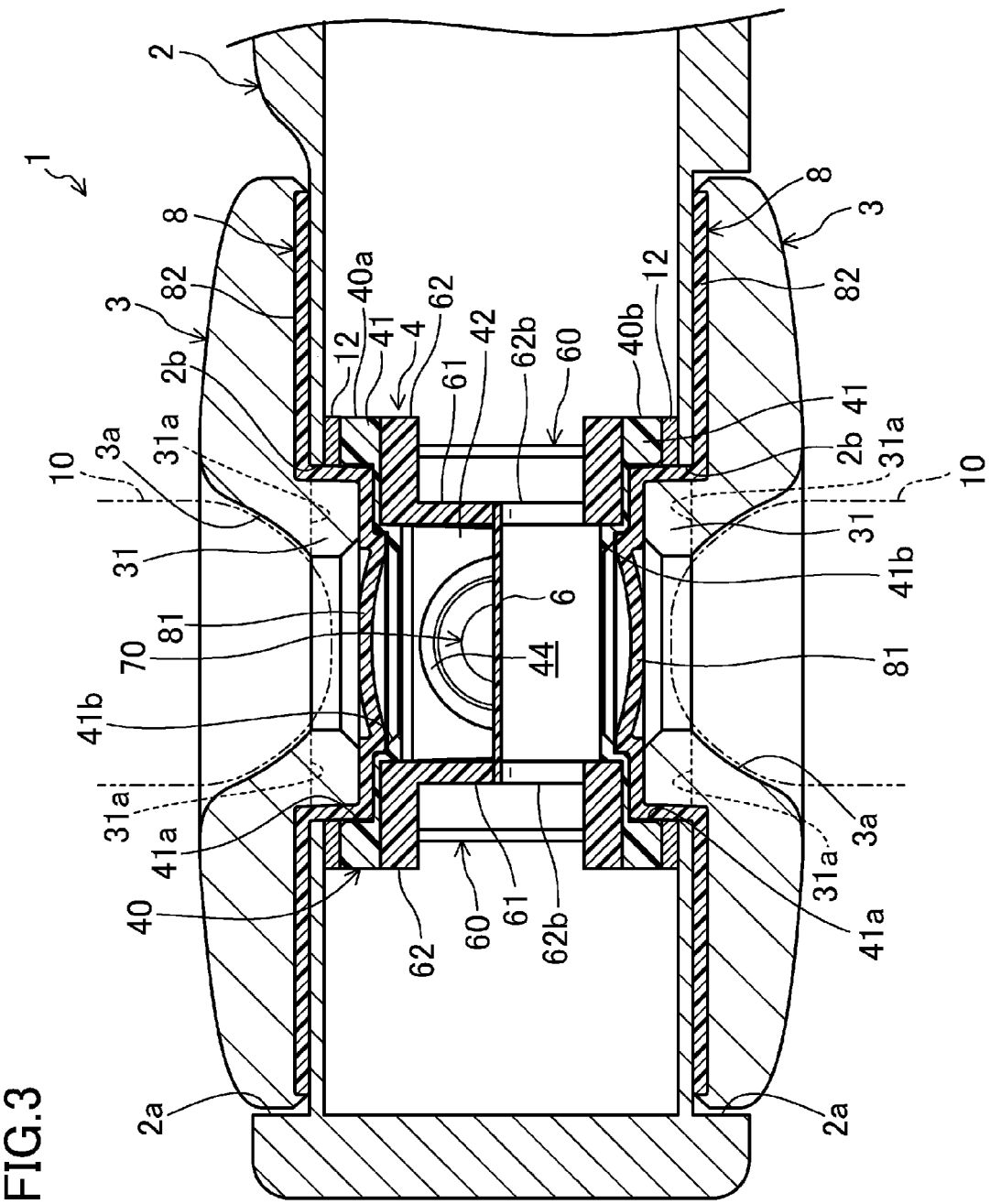
FIG. 3 is a cross-sectional view taken along the line B-B of FIG. 1.

The housing case 2 has a substantially semicircular shape at one longitudinal side. As shown in FIGS. 2 and 3, the upper and lower surfaces of the housing case 2 are recessed to form substantially circular recesses 2a. A circular case opening 2b is formed in the center of each recess 2a.

The both long side surfaces of the housing case 2 are raised as band-like attachment sections 2c extending in the longitudinal direction of the housing case 2. The attachment sections 2c are fixed to a fixed side (not shown) of a production line, thereby attaching the electrode inspection apparatus 1 to the fixed side of the production line.

Substantially circular metal measuring reference plates 3 are detachably attached to the recesses 2a. Electrode fixing holes 3a for inserting and fixing the tips of the electrodes 10 penetrate the measuring reference plates 3 in the center.

Each electrode fixing hole 3a curves gently and reduces the size with the decreasing distance to the front of the corresponding electrode 10 in the insert direction. Each electrode fixing hole 3a faces the corresponding case opening 2b with the measuring reference plate 3 attached to the recess 2a.

In the periphery of the electrode fixing hole 3a of each measuring reference plate 3, a ring projection 31, which can be inserted and fitted to the case opening 2b, protrudes toward the housing case 2 to form a thick portion. A plurality of grooves 31a, which extend radially, are circumferentially formed in the tip surface of the ring projection 31.

At one longitudinal side, the housing case 2 houses a substantially cuboid camera module 4 extending in a direction horizontally intersecting the longitudinal direction of the housing case 2. The camera module 4 includes a resin module body 40, which is the framework of the camera module 4.

At the substantial center of the vertical axis, the module body 40 is divided into a first frame 40a located in a higher position, and a second frame 40b located in a lower position.

The first frame 40a includes a plate-like frame 41 extending horizontally. The center of the upper surface of the plate-like frame 41 is recessed to form a substantially circular recessed portion 41a.

The upper surfaces of the both longitudinal ends of the plate-like frame 41 are recessed to form engaging recesses 41c extending in the longitudinal direction of the housing case 2.

A circular module opening 41b penetrates the recessed portion 41a in the center. The module opening 41b communicates with the case opening 2b to face the electrode fixing hole 3a of each measuring reference plate 3.

A pair of projecting plates 43 extend downward in parallel to interpose the module opening 41b of the plate-like frame 41. A half-split recess 43a recessed upward is formed at the lower end edge of each projecting plate 43.

The lower surface of the plate-like frame 41 is provided with a shield plate 41d projecting along the periphery of the module opening 41b at one longitudinal side of the plate-like frame 41. As shown in FIG. 3, the lower end edge of the shield plate 41d curves gently such that the longitudinal center of the housing case 2 is located in a higher position.

Figure 4:
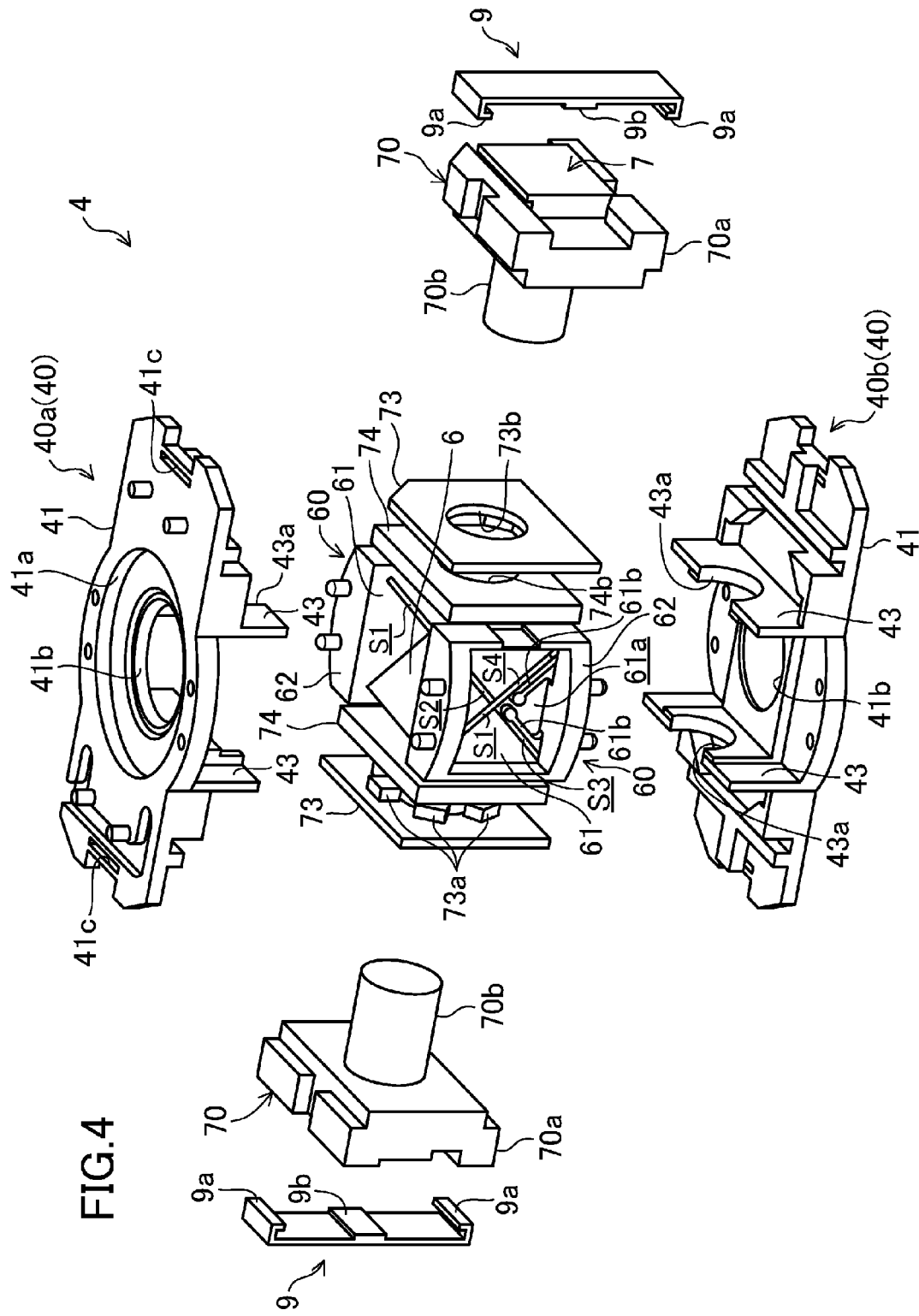
FIG. 4 is an exploded perspective view of a camera module.

As shown in FIGS. 2-4, the second frame 40b has the same structure as the first frame 40a. The same reference characters as those of the first frame 40a are used to represent equivalent elements, and detailed explanation thereof will be omitted.

The module body 40 is assembled by allowing the tips of the projecting plates 43 of the first and second frames 40a and 40b to meet one another such that the shield plates 41d are symmetrical with respect to a point as viewed from side. Once the module body 40 is assembled, the upper and lower projecting plates 43 form bridge frames 42 bridging the plate-like frames 41, and the upper and lower half-split recesses 43a form circular through-holes 44.

A mirror 6 having mirror surfaces at both sides are inclined in the center of the module body 40 between the bridge frames 42. The mirror surfaces of the mirror 6 reflect the tip surfaces of the electrodes 10 inserted into and fixed to the electrode fixing holes 3a.

At the both sides of the mirror 6 in the longitudinal direction of the housing case 2, a pair of resin support frames 60 are located to support the both end edges of the mirror 6.

As shown in FIG. 4, each support frame 60 includes a plate portion 61 formed like a substantially rectangular plate, and a ring-like frame portion 62 projecting outward from the outer periphery of the plate portion 61.

Slits S1 and S2 extending to form a V-shape is formed in the upper half of the plate portion 61. Inverted V-shaped slit S3 and S4 are formed in the lower half as the extensions of the slits S1 and S2. The slits S1-S4 form an X-shape as a whole.

A substantially triangular cut-out 61a is formed in the lower half of the plate portion 61. A pair of flexible rod-like projections 61b extend upward in parallel between the cut-out 61a and the slit S3 and S4 to be inclined such that the distance between the projections 61b gradually decreases from the lower end edge of the cut-out 61a to the tips. Each tip has a substantially circular shape.

The side end edge of the mirror 6 is fitted in the slits S1 and S4. With the side end edge of the mirror 6 fitted in the slits S1 and S4, the rod-like projections 61b bend to increase the width of the slit S4. The resilient force presses the mirror 6 toward the edge forming the slit S4.

While in the embodiments of the present disclosure, the mirror 6 is fitted in the slits S1 and S4, the mirror 6 may be fitted in the slit S2 and S3.

Camera holders 70 are located between the first and second frames 40a and 40b, and at the both ends of the mirror 6.

Each camera holder 70 includes a substantial box-like holder body 70a, and a cylindrical portion 70b projecting from the holder body 70a toward the mirror 6. A housing recess 70c, which is open to the opposite side of the cylindrical portion 70b of the holder body 70a, is formed inside each camera holder 70.

The housing recess 70c houses a CMOS camera 7. The camera 7 captures the tip surface of the electrode 10 reflected by the mirror 6 from the front.

An illuminating plate 73 and a milky white resin diffuser plate 74 are provided at the side of each holder body 70a closer to the mirror 6. A plurality of white LEDs 73a illuminating the tip surface of the electrode 10 reflected by the mirror 6 are attached to the illuminating plate 73. The diffuser plate 74 diffuses light emitted from the white LEDs 73a.

Through-holes 73b and 74b, which correspond to the cylindrical portion 70b, are formed in the illuminating plate 73 and the diffuser plate 74, respectively. The illuminating plate 73 and the diffuser plate 74 are externally fitted in the cylindrical portion 70b.

Flexible band-like resin clips 9 are attached to the both longitudinal ends of the module body 40.

Engaging portions 9a, each of which is folded back toward the corresponding camera holder 70 to form a substantial J-shape, are formed at the upper and lower ends of each clip 9. A projection 9b extends at the center of the clip 9 toward the camera holder 70.

Figure 5:
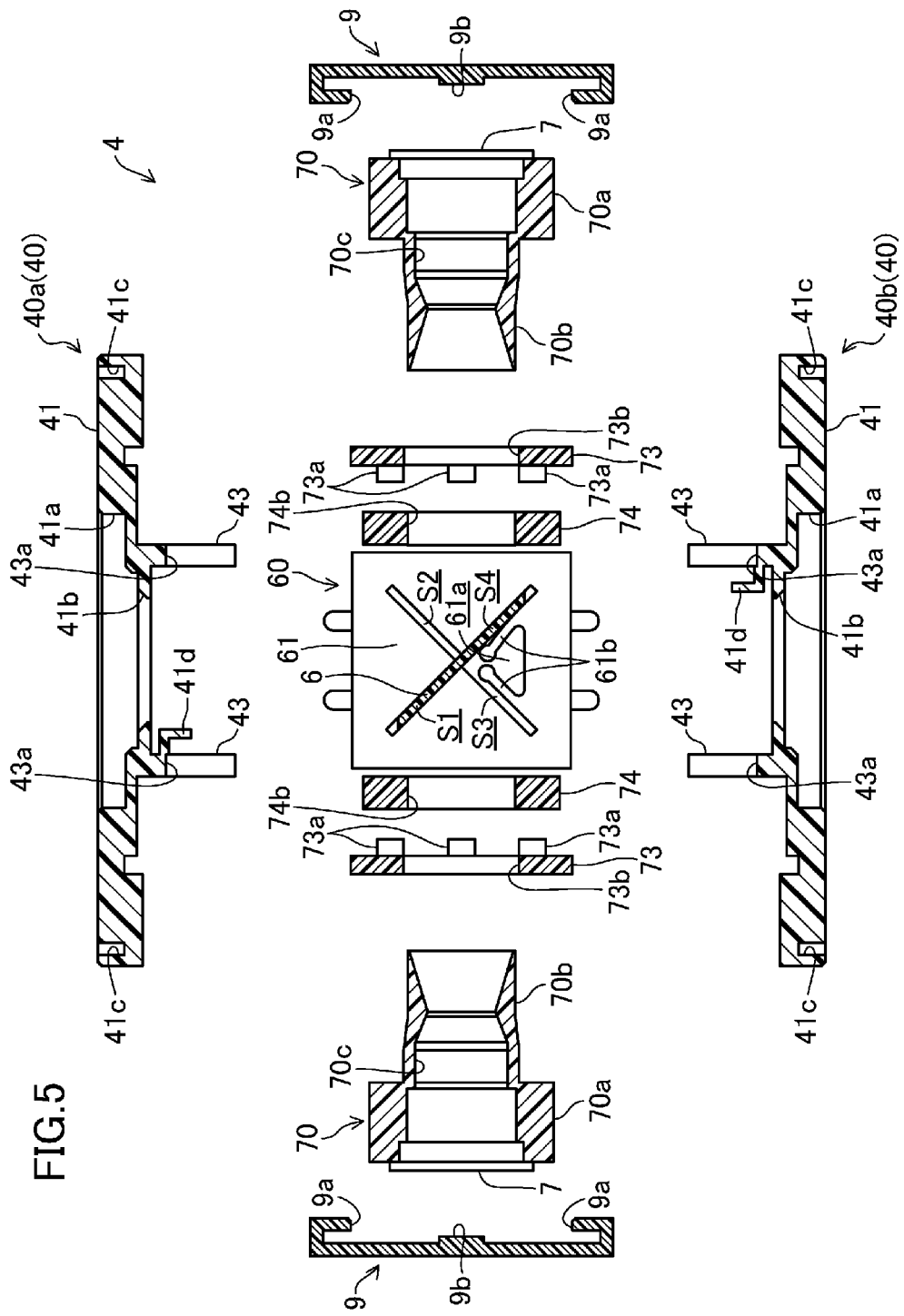
FIG. 5 illustrates a camera module extracted from FIG. 2 immediately before assembling.
Figure 6:
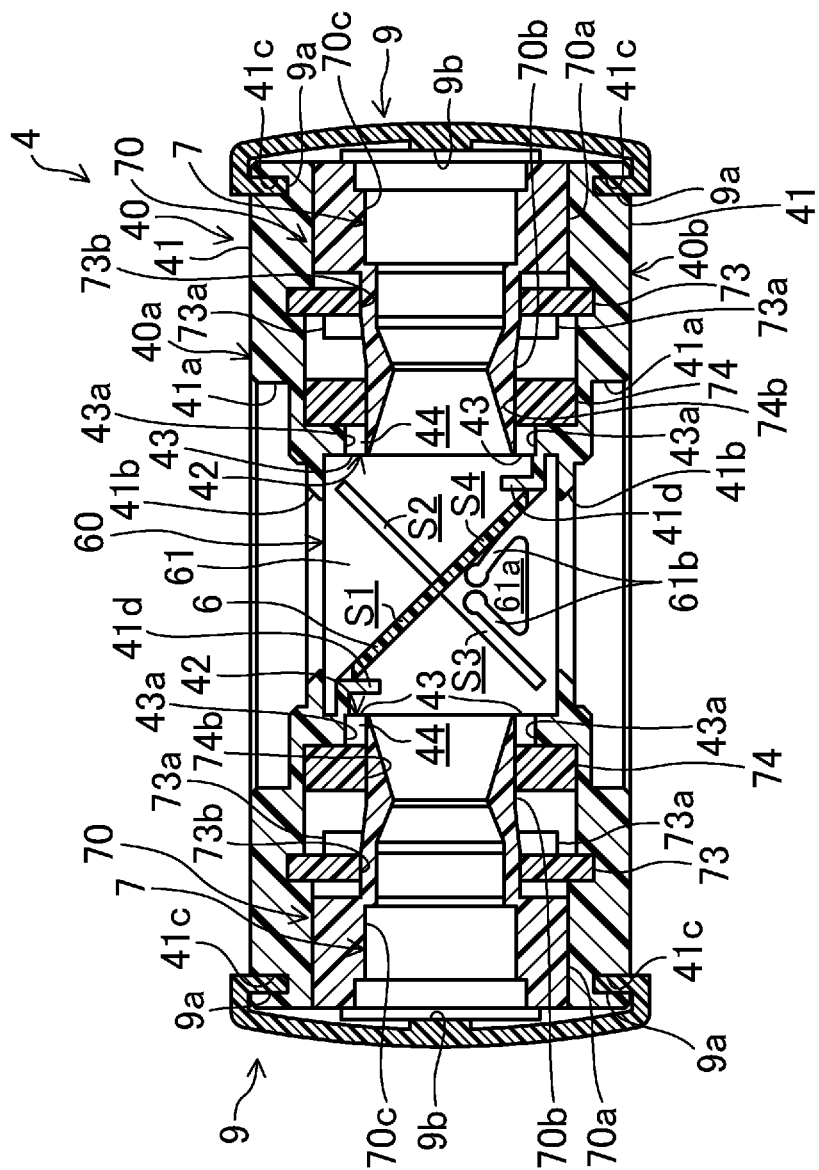
FIG. 6 illustrates the camera module extracted from FIG. 2 immediately after assembling.

As shown in FIGS. 5 and 6, the camera module 4 is assembled in the following manner. The mirror 6 is supported by the pair of support frames 60. The illuminating plates 73 and the diffuser plates 74 are externally fitted in the respective cylindrical portions. The housing recesses 70c house the respective cameras 7. The pair of camera holders 70 are placed with the openings of the housing recesses 70c facing outward. The first and second frames 40a and 40b are placed at the upper and lower sides of the pair of support frames 60 located between the camera holders 70. The both clips 9 are bent such that the engaging portions 9a are engaged with the engaging recesses 41c at the ends edges of the first and second frames 40a and 40b to fix the first frame 40a, the camera holders 70, the support frames 60, the illuminating plates 73, the diffuser plates 74, and the second frame 40b. At the same time, the resilient force of the clips 9 allows the projections 9b to press the cameras 7.

Ring-like light source fixing plates 12, which extend along the outer peripheries of the recessed portions 41a, are placed on the upper and lower surfaces of the module body 40. Blue LEDs 12a are attached to the positions corresponding to the grooves 31a of the light source fixing plates 12.

Light emitted from the blue LEDs 12a passes through the grooves 31a, and radially illuminates the peripheries of the tips of the electrodes 10 fixed to the electrode fixing holes 3a. Panel-like protective covers 8 made of transparent resin are placed on the upper and lower surfaces of the module body 40.

Each protective cover 8 includes a recessed cover body 81 fitted in the corresponding case opening 2b and the corresponding recessed portion 41a, and extensions 82 extending outward from the periphery of the open end of the cover body 81. The extensions 82 are sandwiched between the corresponding measuring reference plate 3 and the housing case 2.

Figure 7:
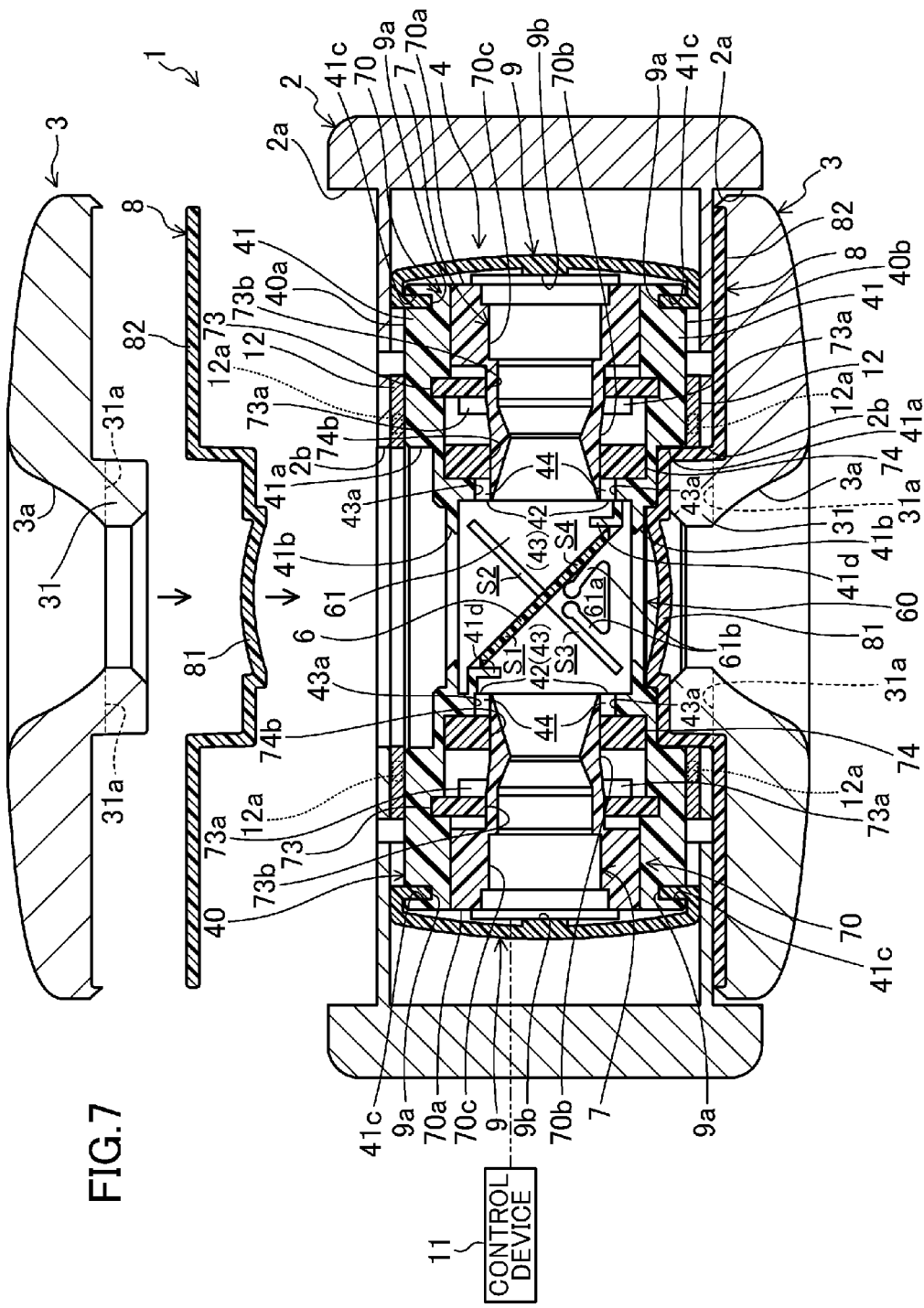
FIG. 7 corresponds to a cross-sectional view taken along the line A-A of FIG. 1 and illustrates exchange of protective covers.

Specifically, each protective cover 8 is interposed between the corresponding measuring reference plate 3 and the housing case 2. As shown in FIG. 7, when the measuring reference plate 3 is attached to the housing case 2, the ring projection 31 is fitted in the recessed portion 41a with the cover body 81 interposed therebetween.

The center of the cover body 81, which corresponds to the module opening 41b, curves gently such that the center is located at the measuring reference plate 3.

Each camera 7 is connected to a control device 11 (i.e., a control section). The control device 11 processes an image of the tip surface of the corresponding electrode 10 captured by the camera 7 via the mirror 6, and compares a result of the processing with a predetermined value to determine whether the tip surface of the electrode 10 is usable.

Next, assembly of the camera module 4 will be described.

First, as shown in FIG. 5, the both side end edges of the mirror 6 are fitted in the slits S1 and S4 of the support frames 60.

Next, the illuminating plates 73 and the diffuser plates 74 are, in this order, externally fitted in the cylindrical portions 70b of the camera holders 70. The housing recesses 70c house the respective cameras 7.

Then, the pair of support frames 60 are placed between the pair of the camera holders 70 with the openings of the housing recesses 70c facing outward. The first and second frames 40a and 40b are placed at the both sides of the both camera holders 70 and the upper and lower sides of the both support frames 60.

After that, the both clips 9 are bent such that the engaging portions 9a are engaged with the engaging recesses 41c of the first and second frames 40a and 40b, thereby fixing the first frame 40a, the camera holders 70, the support frames 60, the illuminating plates 73, the diffuser plates 74, and the second frame 40b. Then, as shown in FIG. 6, the resilient force of the clips 9 allows the projections 9b to press the cameras 7, thereby completing the camera module 4.

As described above, in the embodiment of the present disclosure, the clips 9 clip the first and second frames 40a and 40b together to integrate the first frame 40a, the camera holders 70, and the second frame 40b. With the first frame 40a, the camera holders 70, and the second frame 40b integrated, the projections 9b of the clips 9 press the cameras 7 toward the camera holders 70. By using the clips 9 as fixing means of the components of the camera module 4, the first and second frames 40a and 40b are fixed to the camera holders 70, and the cameras 7 are fixed to the camera holders 70 at once. A short time is required to assemble the camera module 4, as compared to the case using an adhesive or screws. Since there is no need to form fastening portions in the components to fix the first frame 40a, the camera holders 70, and the second frame 40b together, the camera module 4 can be miniaturized. After the camera module 4 is assembled, the resilient force of the clips 9 always presses the cameras 7 toward the camera holders 70. In using the electrode inspection apparatus 1, the cameras 7 are not displaced relative to the first and second frames 40a and 40b, thereby causing no or less erroneous determination of the electrode inspection apparatus 1.

Since the tips of the projections 9b of the clips 9 abut on the cameras 7 after the camera module 4 is assembled, the projections 9b reliably transmit the resilient force of the bent clips 9 to the cameras 7, thereby fixing the cameras 7 to the camera holders 70 more firmly.

When the clips 9 clip the first and second frames 40a and 40b, not only the camera holders 70 but also the both support frames 60 supporting the mirror 6 are sandwiched between the first and second frames 40a and 40b and integrally fixed. Therefore, by using the clips 9 to assemble the camera module 4, the mirror 6 can be mounted between the first and second frames 40a and 40b at the same time as fixing the first frame 40a, the camera holders 70, and the second frame 40b. As a result, the camera module 4 is assembled more simply.

In addition, when the measuring reference plates 3 are attached to the housing case 2, the ring projections 31 are fitted in the recessed portions 41a formed in the camera module 4. That is, the positioning of the measuring reference plates 3 is determined not with respect to the housing case 2 but to the camera module 4. The electrode fixing holes 3a are thus not displaced relative to the mirror 6, when the measuring reference plates 3 are attached to the housing case 2 after being detached from the housing case 2 to exchange the protective covers 8. This does not change the positions of the tip surfaces of the electrodes 10, whose images are captured by the cameras 7, before and after exchanging the protective covers 8. No or less erroneous determination of the electrode inspection apparatus 1 occurs due to the exchange of the protective covers 8. Furthermore, since the ring projections 31 increase the thicknesses of the measuring reference plates 3 in the peripheries of the electrode fixing holes 3a, the stiffness of the thick portions increases to reduce deformation in abutting on the electrodes 10. The positioning of the electrodes 10 does not change due to the deformation in the peripheries of the electrode fixing holes 3a, thereby reducing positional changes of the tip surfaces of the electrodes 10, whose images are captured by the cameras 7. This also causes no or less erroneous determination of the electrode inspection apparatus 1.

At the side closer to the housing case 2, each measuring reference plate 3 abuts on the corresponding protective cover 8, with the measuring reference plate 3 attached to the housing case 2. This allows less dust etc., to enter the housing case 2 between the measuring reference plate 3 and the protective cover 8, thereby reducing malfunction of the electrode inspection apparatus 1 due to the dust etc., entering the housing case 2.

In the first embodiment of the present disclosure, the projection 9b is located in the middle of each clip 9. Alternatively, no projection 9b may be provided in the middle of the clip 9. The middle of each clip 9 without projection 9b may abut on the corresponding camera 7 in assembling the camera module 4.

In the first embodiment of the present disclosure, after the both side end edges of the mirror 6 are supported by the pair of support frames 60, the both support frames 60 are sandwiched between the first and second frames 40a and 40b to mount the mirror 6 between the first and second frames 40a and 40b. Alternatively, after the both support frames 60 not supporting the mirror 6 is sandwiched between the first and second frames 40a and 40b, the mirror 6 may be fitted in the slits S1 and S4 of the both support frames 60 from the sides to mount the mirror 6 between the first and second frames 40a and 40b.

While in the first embodiment of the present disclosure, the ring projections 31 are fitted in the recessed portions 41a with the protective covers 8 interposed therebetween, the structure is not limited thereto. The ring projections 31 may be directly fitted in the recessed portions 41a without interposing the protective covers 8.

In order to further reduce the dust etc., entering the housing case 2, sealing structures such as O-rings may be placed between each protective cover 8 and the module body 40, and between each protective cover 8 and the corresponding measuring reference plate 3.

Second Embodiment

Figure 8:
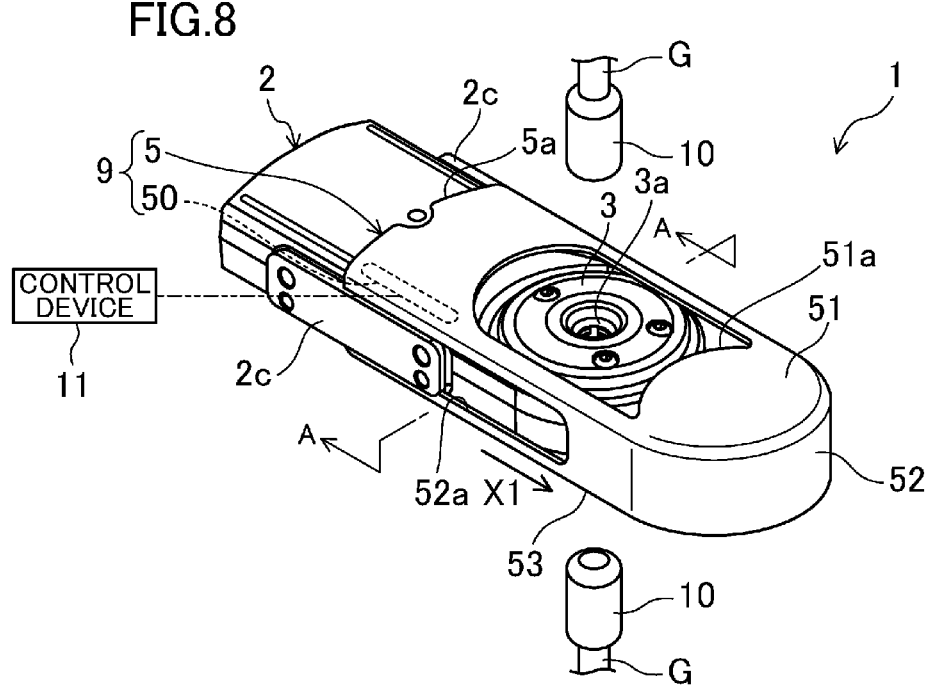
FIG. 8 is a perspective view of an electrode inspection apparatus for spot welding according to a second embodiment of the present disclosure, immediately before inspecting an electrode.
Figure 9:
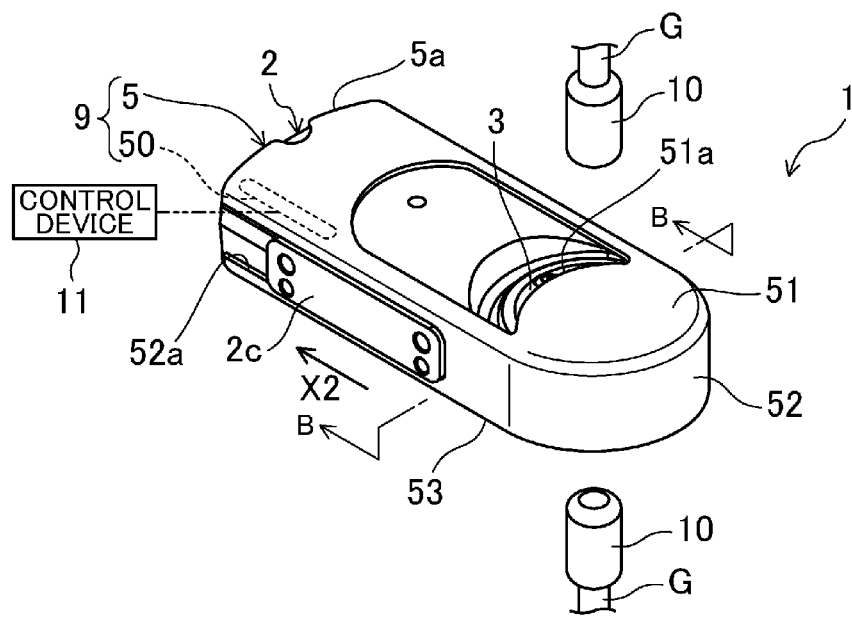
FIG. 9 is a perspective view of the electrode inspection apparatus for spot welding according to the second embodiment, while inspecting a protective cover.

FIGS. 8 and 9 illustrate an electrode inspection apparatus 1 for spot welding according to a second embodiment of the present disclosure. Different from the first embodiment, in this second embodiment, the control device 11 for determining whether or not the tip surfaces of the electrodes 10 are usable is also used for determining whether or not the protective covers 8 are usable. In other respects, this embodiment is the same as the first embodiment. Only the differences from the first embodiment will be described.

The electrode inspection apparatus 1 for spot welding according to the second embodiment includes a cover case 5 protecting the housing case 2.

The cover case 5 is formed like a flat cuboid corresponding to the exterior of the housing case 2, and includes a panel-like upper wall 51, a lower wall 53, and a side wall 52 connecting the upper and lower walls.

One longitudinal end of the cover case 5 is closed, while a side opening 5a is formed in the other longitudinal end. Inside the cover case 5, a housing space S, into which the housing case 2 provided with the measuring reference plates 3 is inserted from the side opening 5a, includes the upper wall 51, the side wall 52, and the lower wall 53.

Substantially rectangular cover openings 51a and 53a are formed in the centers of the upper wall 51 and the lower wall 53, respectively. A pair of long and narrow guide sections 52a are formed at the long sides of the side wall 52 of the cover case 5 to extend in the longitudinal direction of the cover case 5 and to be open toward the side opening 5a.

The cover case 5 slides toward the housing case 2 (in the direction indicated by an arrow X2 of FIG. 9) such that the side opening 5a of the cover case 5 corresponds to one longitudinal end of the housing case 2 and the openings of the guide sections 52a correspond to the attachment sections 2c. As a result, while the guide sections 52a guide the attachment section 2c, the housing space S houses the housing case 2.

That is, the cover case 5 slides to intersect the direction of inserting the electrodes 10 into the electrode fixing holes 3a. The sliding operation of the cover case 5 moves the housing case 2 in and out of the housing space S.

The cover case 5 slides toward the other longitudinal end of the housing case 2 (in the direction indicated by the arrow X2 of FIG. 9) to house the housing case 2 in the housing space S. In this state, the one longitudinal ends of the upper wall 51 and the lower wall 53 of the cover case 5 are located at the positions closing the electrode fixing holes 3a, thereby closing the electrode fixing holes 3a. On the other hand, the cover case 5 slides toward the one longitudinal end of the housing case 2 (in the direction indicated by an arrow X1 of FIG. 8) to expose part of the housing case 2 from the housing space S. In this state, the cover openings 51a and 53a of the upper wall 51 and the lower wall 53 correspond to the electrode fixing holes 3a, thereby opening the electrode fixing holes 3a.

In short, the sliding operation of the cover case 5 moves the cover openings 51a and 53a of the cover case 5 between the positions corresponding to the electrode fixing holes 3a, and the positions deviating from the electrode fixing holes 3a.

A drive section 50 is provided between the housing case 2 and the upper wall 51. The drive section 50 and the cover case 5 form an opening-closing mechanism (i.e., an opening-closing section) 13.

Although not shown, the drive section 50 includes a rack, a pinion, and a drive motor. The drive section 50 drives to slide the cover case 5 in the longitudinal direction of the housing case 2.

The drive section 50 is connected to a control device 11. The control device 11 outputs capture operation signals to the cameras 7, and outputs opening-closing operation signals to the drive section 50 to slide the cover case 5.

The control device 11 outputs an opening operation signal to the drive section 50 to slide the cover case 5 toward the one end of the housing case 2, thereby opening the electrode fixing holes 3a. With the electrodes 10 inserted into and fixed to the electrode fixing holes 3a, the control device 11 outputs a capture operation signal to the cameras 7, thereby allowing the cameras 7 to capture the tip surfaces of the electrodes 10 via the mirror 6.

The control device 11 processes images of the tip surfaces of the electrodes 10 captured by the cameras 7 and compares a result of the processing with predetermined values of the tip surfaces of the electrodes 10 to determine whether or not the tip surfaces of the electrodes 10 are usable.

On the other hand, the control device 11 outputs a closing operation signal to the drive section 50 to slide the cover case 5 toward the other end of the housing case 2, thereby closing the electrode fixing holes 3a, and outputs a capture operation signal to the cameras 7, thereby allowing the cameras 7 to capture the protective covers 8 via the mirror 6.

The control device 11 processes images of the protective covers 8 captured by the cameras 7 and compares a result of the processing with predetermined values of the protective covers 8 to determine whether or not the protective covers 8 are usable.

As described above, in the second embodiment of the present disclosure, the control device 11 for determining whether or not the tip surfaces of the electrodes 10 are usable is used to determine whether or not the protective covers 8 are usable. As a result, the operator figures out the contamination degree of the protective covers 8 outside the production line. Therefore, the protective covers 8 can be exchanged at proper timing to reduce erroneous determination of the electrode inspection apparatus 1 caused by excessive dirt of the protective covers 8. In addition, the production line is stopped for a minimum time period necessary for exchanging the protective covers 8, thereby reducing drop in the operating rate of the production line caused by the exchange of the protective covers 8.

When the protective covers 8 are captured with the electrode fixing holes 3a covered with the cover case 5, the cover case 5 serves as the background to clarify the captured images even if the protective covers 8 are transparent. This allows the control device 11 to analyze the images accurately, thereby reliably reducing erroneous determination.

Since the cover case 5 covers the electrode fixing holes 3a, dust etc., is difficult to pass through the electrode fixing holes 3a and enter the housing case 2. This retards contamination of the protective covers 8, and reduces the time intervals of exchanging the protective covers 8, thereby increasing the operating rate of the production line.

In addition, the cover case 5 slides to intersect the direction of inserting the electrodes 10 into the electrode fixing holes 3a. Even when the cover case 5 moves the electrode fixing holes 3a from the closed positions to the open positions, with the electrodes 10 placed near the electrode fixing holes 3a, the electrodes 10 does not abut on the cover case 5. This reduces the period between the time of opening the electrode fixing holes 3a with the cover case 5 to the time of inserting the electrodes 10 into the electrode fixing holes 3a. Furthermore, dust etc., is difficult to pass through the electrode fixing holes 3a and enter the housing case 2, thereby retarding contamination of the protective covers 8.

The cover case 5 covers the entire housing case 2, thereby protecting the entire exterior of the housing case 2. Furthermore, since the cover case 5 for protecting the exterior of the housing case 2 is used to open and close the electrode fixing holes 3a, there is no need to add any components for opening and closing the electrode fixing holes 3a other than the cover case 5. The structure is formed simply at low costs.

While in the second embodiment of the present disclosure, the housing space S houses the entire housing case 2, the structure is not limited thereto. The housing space S may cover at least the region of the housing case 2, to which the measuring reference plates 3 are attached, including the electrode fixing holes 3a.

Third Embodiment

Figure 10:
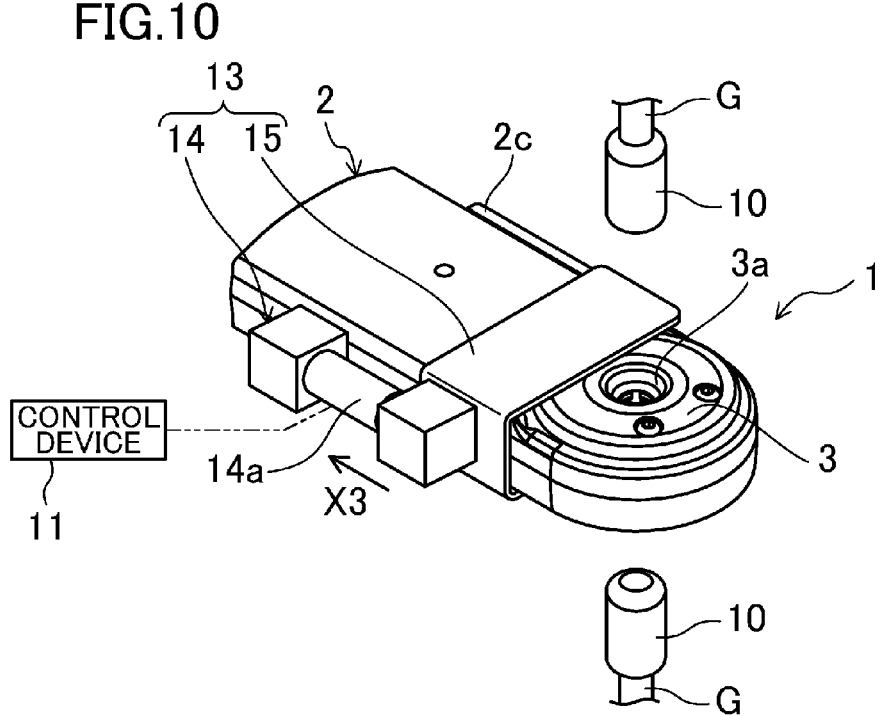
FIG. 10 illustrates a third embodiment of the present disclosure, and corresponds to FIG. 8.
Figure 11:
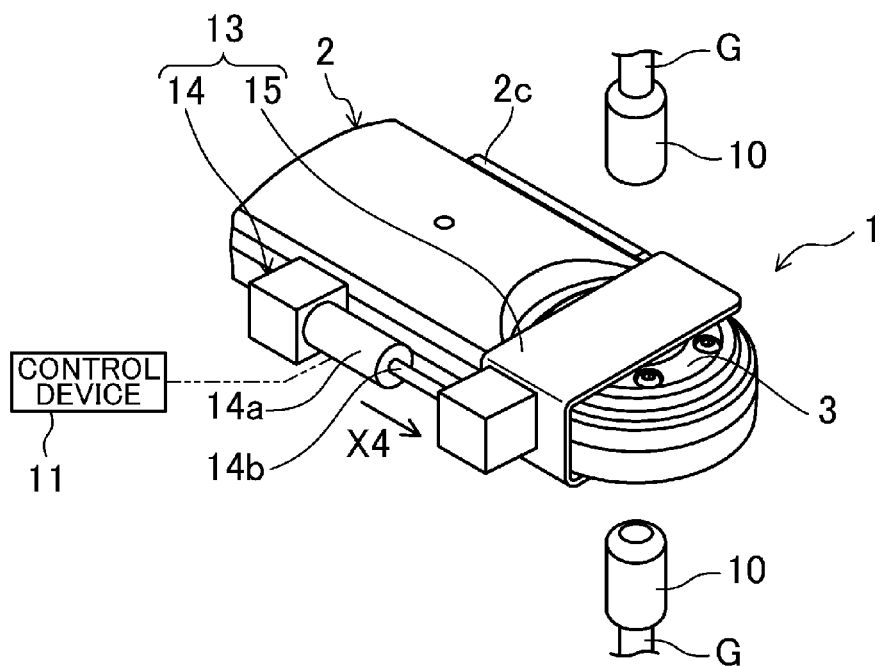
FIG. 11 illustrates the third embodiment, and corresponds to FIG. 9.

FIG. 10 and FIG. 11 illustrate an electrode inspection apparatus 1 for spot welding according to a third embodiment of the present disclosure. The third embodiment merely differs from the second embodiment in the structure of the opening-closing mechanism 13. In other respects, this embodiment is the same as the second embodiment. Differences from the second embodiment will be described.

In the third embodiment, an air cylinder 14 extending in the longitudinal direction of the housing case 2 is formed at one of the long sides of a housing case 2.

The air cylinder 14 includes a cylinder body 14a, and a rod 14b stretchable from one longitudinal end of the cylinder body 14a along the body of the inspection apparatus. The other longitudinal end of the cylinder body 14a is fixed to the housing case 2.

A substantially U-shaped cover plate 15 divided into two in the direction intersecting the longitudinal direction of the housing case 2 is attached to the tip of the rod 14b. One of the two divided portions of the cover plate 15 is located at the front surface of the housing case 2, and the other is located at the back surface of the housing case 2.

The opening-closing mechanism 13 according to the third embodiment includes the air cylinder 14 and the cover plate 15. When the rod 14b extends, the cover plate 15 slides toward one longitudinal end of the housing case 2 (in the direction indicated by an arrow X4 of FIG. 11) to move to the position closing the electrode fixing holes 3a, thereby closing the electrode fixing holes 3a. When the rod 14b shrinks, the cover plate 15 slides toward the other longitudinal end of the housing case 2 (in the direction indicated by an arrow X3 of FIG. 10) to move to the position opening the electrode fixing holes 3a, thereby opening the electrode fixing holes 3a.

A control device 11 is connected to the air cylinder 14 to output opening-closing signals to allow the air cylinder 14 to slide the cover plate 15.

As described above, the third embodiment of the present disclosure provides the electrode inspection apparatus 1 including the opening-closing mechanism 13 having the structure more simple than that of the second embodiment. This structure reduces erroneous determination caused by contamination of protective covers 8, and reduces drop in the operating rate of the production line caused by the exchange of the protective covers 8 as much as possible.

The present disclosure is suitable, for example, for electrode inspection apparatuses for spot welding used in automobile production lines.

What is claimed is:

1. An electrode inspection apparatus for spot welding comprising:
    measuring reference plates, each having an electrode fixing hole for inserting and fixing a tip of an electrode for spot welding; and
    a camera module, wherein
    the camera module includes
        a first frame having an engaging recess at each longitudinal end,
        a second frame provided in parallel to the first frame, and having an engaging recess at each longitudinal end,
        a pair of flexible band-like clips, one being located between one longitudinal ends of the first and second frames, the other being located between the other longitudinal ends of the first and second frames, and each having an engaging portion at each end,
        a mirror located between the first and second frames, and configured to reflect a tip surface of the electrode,
        a pair of cameras, each being located at one side of the mirror between the first and second frames, and configured to capture the tip surface of the electrode reflected by the mirror,
        a pair of camera holders, each having a housing recess for housing associated one of the cameras, and
    the camera module is assembled by bending the both ends of one of the clips toward the first and second frames, with a middle of the one of the clips abutting on one of the cameras, to engage the engaging portions of the one of the clips with the engaging recesses at one longitudinal ends of the first and second frames, bending the both ends of the other one of the clips toward the first and second frames, with a middle of the other one of the clips abutting on the other one of the cameras, to engage the engaging portions of the other one of the clips with the engaging recesses at the other longitudinal ends of the first and second frames, while housing the cameras in the respective housing recesses, and allowing respective openings of the housing recesses to face the clips, to press the cameras onto the respective camera holders using resilient force of the clips, while interposing the camera holders between the first and second frames using the clips, and
    the tip of the electrode is inserted into and fixed to the electrode fixing hole, with each of the measuring reference plates attached to the camera module such that the electrode fixing hole corresponds to the mirror, and the camera captures the tip surface of the electrode via the mirror to determine whether or not the tip surface of the electrode is usable.

2. The electrode inspection apparatus for spot welding of claim 1, wherein
    a projection is formed in the middle of each of the clips at a side close to the camera holder.

3. The electrode inspection apparatus for spot welding of claim 1, wherein
    the camera module includes a pair of support frames configured to support both side end edges of the mirror, interposed, and fixed between the first and second frames.

4. The electrode inspection apparatus for spot welding of claim 1, further comprising:
    a housing case configured to house the camera module, wherein
    the camera module includes a transparent protective cover,
    the measuring reference plates are detachably attached to the housing case,
    communicating openings corresponding to the mirror are formed in the housing case and the module body to face the electrode fixing hole of each of the measuring reference plates,
    the protective cover is interposed between each of the measuring reference plates and the housing case to cover the openings,
    a ring projection projects in a periphery of the electrode fixing hole of each of the measuring reference plates toward the housing case to form a thick portion, and
    a fitting portion, in which the ring projection is fitted, is formed in a periphery of the opening of the module body.

5. The electrode inspection apparatus for spot welding of claim 1, wherein a protective cover is formed like a panel, and includes a recessed cover body fitted in an opening of the housing case, and a fitting portion of the module body, and an extension extending outward from a periphery of an opening end of the cover body, and sandwiched between each of the measuring reference plates and the housing case.

6. The electrode inspection apparatus for spot welding of claim 1, further comprising:

an opening-closing section located outside the protective cover, and configured to open and close the electrode fixing hole; and a control section connected to the camera and the opening-closing section, configured to output a capture operation signal to the camera and opening-closing operation signals to the opening-closing section, wherein the control section outputs an opening operation signal to the opening-closing section to open the electrode fixing hole, outputs a capture operation signal to the camera with the electrode inserted into and fixed to the electrode fixing hole to capture the electrode tip surface with the camera via the mirror, processes an captured image of the tip surface of the electrode, and compares a result of processing with a predetermined value of the tip surface of the electrode to determine whether or not the electrode tip surface is usable, and the control section outputs an closing operation signal to the opening-closing section to close the electrode fixing hole, outputs a capture operation signal to the camera to capture the protective cover with the camera via the mirror, processes an captured image of the protective cover, and compares a result of processing with a predetermined value of the protective cover to determine whether or not the protective cover is usable.

7. The electrode inspection apparatus for spot welding of claim 6, wherein the opening-closing section is slidable to intersect a direction of inserting the electrode into the electrode fixing hole, and a sliding operation switches the electrode fixing hole between an open position and a closed position.

8. The electrode inspection apparatus for spot welding of claim 7, wherein the opening-closing section includes a housing space configured to house the housing case, to which the measuring reference plates are attached, from one side to a region including the electrode fixing hole, and a slidable cover case having an opening corresponding to the electrode fixing hole, and the cover case performs sliding operation to move between a position in which the opening corresponds to the electrode fixing hole, and a position in which the opening deviates from the electrode fixing hole.

9. The electrode inspection apparatus for spot welding of claim 2, wherein the camera module includes a pair of support frames configured to support both side end edges of the mirror, interposed, and fixed between the first and second frames.

* * * * *